(12) United States Patent
Romé et al.

(10) Patent No.: US 7,910,511 B2
(45) Date of Patent: Mar. 22, 2011

(54) METHOD OF PREPARING METALLIC NANOPARTICLES AND MATERIALS THUS OBTAINED

(75) Inventors: Julio Santarén Romé, Madrid (ES); Francisco Javier Limpo Orozco, Madrid (ES); Eduardo Aguilar Díez, Madrid (ES); Antonio Álvarez Berenguer, Madrid (ES); José Moya Corral, Madrid (ES); Carlos Pecharroman Garcia, Madrid (ES)

(73) Assignee: Tolsa, S.A., Madrid (ES)

( * ) Notice: Subject to any disclaimer, the term of this patent is extended or adjusted under 35 U.S.C. 154(b) by 0 days.

(21) Appl. No.: 12/802,970

(22) Filed: Jun. 17, 2010

(65) Prior Publication Data

US 2010/0261005 A1 Oct. 14, 2010

Related U.S. Application Data

(60) Division of application No. 11/403,140, filed on Apr. 12, 2006, now Pat. No. 7,829,493, which is a continuation of application No. PCT/ES2004/000441, filed on Oct. 15, 2004.

(30) Foreign Application Priority Data

Oct. 15, 2003 (ES) .................................. 200302396

(51) Int. Cl.
*B01J 21/16* (2006.01)
*B01J 23/40* (2006.01)
*B01J 23/70* (2006.01)
*B32B 5/16* (2006.01)

(52) U.S. Cl. ................. 502/80; 502/74; 502/81; 502/84; 502/85; 502/87; 502/258; 977/773; 977/775

(58) Field of Classification Search .................... 502/80, 502/81, 84, 85, 87, 74, 258; 977/779, 775
See application file for complete search history.

(56) References Cited

U.S. PATENT DOCUMENTS

| | | | | |
|---|---|---|---|---|
| 6,641,973 B1 * | 11/2003 | Dontula et al. | ............... | 430/201 |
| 7,046,439 B2 * | 5/2006 | Kaminsky et al. | ............. | 359/452 |
| 7,053,021 B1 * | 5/2006 | Zhong et al. | .................. | 502/185 |
| 7,335,245 B2 * | 2/2008 | He et al. | ......................... | 75/351 |
| 2005/0031982 A1 * | 2/2005 | Rao et al. | ...................... | 430/201 |
| 2005/0211259 A1 * | 9/2005 | Gedevanishvili | ............. | 131/334 |

FOREIGN PATENT DOCUMENTS

| | | |
|---|---|---|
| EP | 0 170 299 | 2/1986 |
| EP | 0 454 222 A1 | 10/1991 |
| EP | 1 002 574 A1 | 5/2000 |
| JP | 07173022 A | 7/1995 |

OTHER PUBLICATIONS

Flytzanis, C. et al, Nonlinear Optics in Composite Materials, Prog. Optics, 29, 322 (1991).
B.D. Cullity, Introduction to Magnetic Materials, Addison-Wesley, California, 1972, 117-119 and 309-311.
J.I. Gittleman et al, Phys. Rev. B, 5, 3609 (1972).
H. Gleiter, Progress in Mater. Sco., 33, 223 (1989).
V.G. Gryzanov et al, Progress Mater. Sco., 37, 289 (1993).
Eric Gaffet et al, Some Recent Developments in Mechanical Activation and Mechanosynthesis, Journal of Material Chemistry, 9, 305-314 (1998).
D.G. Morris, Mechanical Behavior of Nanostructured Materials, vol. 2 of Materials Science Foundations, Trans Tech Publications Ltd. (1998).
F. Ebrahimi et al, Nanostruct. Mater., 1999, 11, 343.
S.J. Veprek, Vac. Sci. Technol. A, 1999, 17, 2401.
Philip Moriarty, Nanostructured Materials, Reports on Progress in Physics, 64, 297-381 (2001).
J. Musil, et al, Surf. Coat. Tech, 115, 32-37 (1999).
K. Niihara, New Design Concept of Structural Ceramics-Ceramic Nanocomposites, J. Ceram. Soc. Jpn, 99 (1991) 974.
S.T. Oh et al, Mechanical and magnetic properties of Ni-Co dispersed $Al_2O_3$ nanocomposites, J. Mater. Sci. 36 (2001) 1817.
T. Sekino et al, Microstructural characteristics and mechanical properties for $Al_2O_3$/metal nanocomposites, Nanostructural Materials, vol. 6 (1995) 663.
T. Sekino et al, Reduction and Sintering of a Nickel-Dispersed-Alumina Composite and its Properties J. Am. Ceram. Soc., 80, 5 (1997) 1139.
M. Nawa et al, Fabrication and Mechanical Properties of $Al_2O_3$/Mo Nanocomposites, J. Mater. Sci., 29 (1994) 3185.
S.T. Oh et al, Fabrication and Mechanical Properties of 5% vol Copper Dispersed Alumina Nanocomposite, J. Eur. Ceram., Soc., 18 (1998) 31.
R.Z. Chen et al, Pressureless Sintering of $Al_2O_3$/Ni Nanocomposites, J. Eur. Ceram. Soc., 19 (1999) 463.
T. Sekino et al, Nanocomposite Structural Ceramic with Advanced Properties, Proc. 4$^{th}$ Japan International SAMPE (1995).
Aramendia, M.A. et al, Selective Liquid-Phase Hydrogenation of Citral over Supported Palladium, Journal of Catalysis, Nov. 1977, vol. 172, pp. 46-54.

* cited by examiner

*Primary Examiner* — Elizabeth D Wood
(74) *Attorney, Agent, or Firm* — Klauber & Jackson LLC

(57) ABSTRACT

The invention relates to a method of preparing metallic nanoparticles and to the materials thus obtained. More specifically, the invention relates to a method of preparing metallic nanoparticles consisting in: selecting a precursor from the salts, hydroxides and oxides of metallic elements that can be reduced at temperatures below the clay silicate network destruction temperature; and depositing said precursor on a support selected from pseudolaminar phyllosilicate clays. According to the invention the method comprises: (i) a deposition step in which the precursor is deposited on the support: (ii) when the precursor is selected from among salts and hydroxides, a thermal decomposition step in a controlled atmosphere, in which the precursor is subjected to a decomposition process and is transformed into an oxide of the metallic element: and (iii) a reduction step in which the oxide of the metallic element is subjected to a reduction process in a controlled atmosphere. The aforementioned method is performed at temperatures below the clay silicate network destruction temperature.

8 Claims, 11 Drawing Sheets

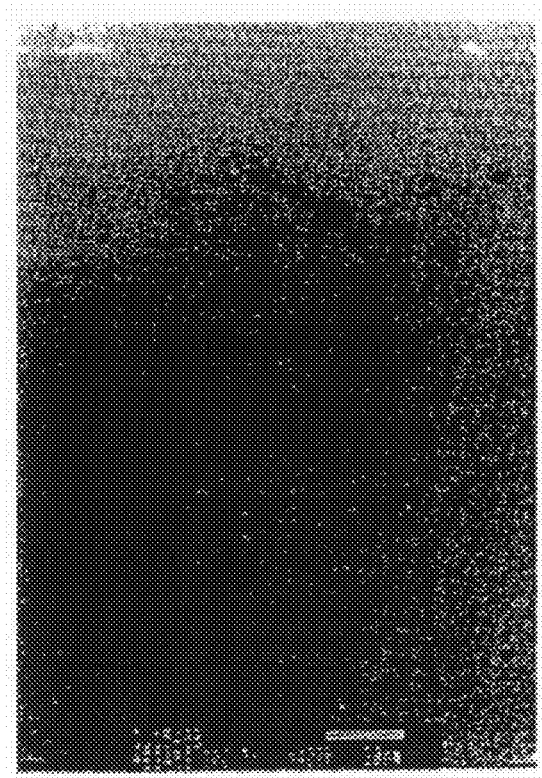 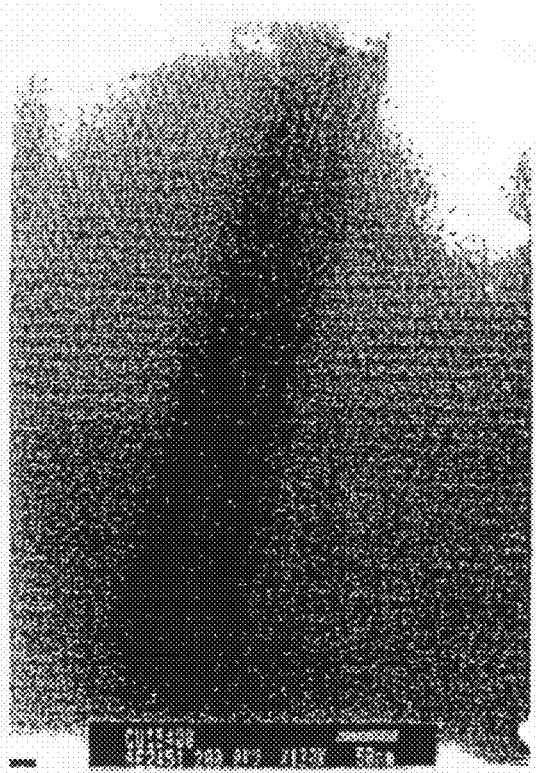
FIG. 1A                    FIG. 1B

METHOD OF PREPARING METALLIC NANOPARTICLES AND MATERIALS THUS OBTAINED

RELATED APPLICATIONS

The present application is a division of U.S. Ser. No. 11/403,140, filed Apr. 12, 2006, now U.S. Pat. No. 7,829,493, which is a continuation of Co-pending PCT Application No. PCT/ES2004/000441, filed on Oct. 15, 2004, which in turn, claims priority from Spanish Application Serial No. 200302396, filed on Oct. 15, 2003. Applicants claim the benefits of 35 USC §120 as to the PCT application, and priority under 35 USC §119 as to the Spanish Application, and the entire disclosures of all three applications are incorporated herein in their entireties.

TECHNICAL FIELD OF THE INVENTION

The present invention refers generally to the nanoparticles field, particularly to the field of metallic nanoparticles, and more especially to the area of nanoparticles homogeneously dispersed over supports.

PRIOR ART

Nanomaterials or nanostructured materials are heterogeneous systems constituted by particles which size ranges between 1 and 100 mm ($10^{-9}$ to $10^{-7}$ m). These systems have physical properties that can be very different from those found in equivalent systems which size is that of a micrometric grain. Amongst the most notable physical properties that appear at the nanometric scale are the quantization phenomena (charge, electronic levels . . . ); the confining phenomena (electronic, dielectric [Flytzanis, C., Hache, F., Kelin, M. C., Ricard, D., and Roussignol, Ph., "Nonlinear Optics in Composite Materials", Prog. Optics, 29, 322 (1991)]; the presence of monodomains (crystalline, ferromagnetic [B. D. Cullity. "Introduction to Magnetic Materials", Addison-Wesley, California, 1972, 117-119 and 309-311], ferroelectrical); giant magnetorresistance effect [J. I. Gittleman, Y. Goldstein, and S. Bozowski, Phys. Rev. B 5 3609 (1972)]; Hall-Petch effect or suppression of dislocation pileups, [H. Gleiter, Progress in Mater. Sci., 33, 223 (1989); V. G. Gryzanov and L. I. Trusov, Progress Mater. Sci., 37 289 (1993)], etc.

Currently there is a great effort in global R+D focused both on the production and the characterization of these nanoparticled materials with the further objective to manufacture new products and devices.

Particularly, the metallic nanoparticles are one of the most studied nanomaterials since they display physical properties that are unique to insulators and conductors or a mixture of both [H. Gleiter, Progress in Mater. Sci., 33, 223 (1989), V. G. Gryaznov and L. I Trusov, Progress Mater. Sci., 37 289 (1993)]. These materials are currently being used in colloidal and catalysis chemical processes. On the other hand the expectation is that in the near future metallic nanomaterials may be used to manufacture "opto" and/or electronic devices.

Currently, the synthesis of nanoparticles is achieved by several methods, such as: mechanical activation [Eric Gaffet, Fréderic Bernad, Jean-Claude Niepce, Fréderic Charlot, Chirstophe Gras, Gérard Le Caér, Jean-Louis Guichard, Pierre Delcroix, Alain Mocellin and Olivier Tillement. "Some Recent Developments in Mechanical Activation and Mechanosynthesis", Journal of Material Chemistry, 9, 305-314 (1998)]; wet synthesis methods (hydrothermal and thermal decomposition of the precursor material), sol-gel [D. G. Morris, "Mechanical Behavior of Nanostructured Materials", Vol. 2 of Materials Science Foundations, Trans Tech Publications Ltd, (1998)]; synthesis during the gaseous phase, electrochemical methods [Ebrahimi, F. Bourne, G. R. Kelly, M. S, and Matthews, T. E., Nanostruct. Mater., 1999, 11 343]; chemical epitaxial growth (Veprek, S. J., Vac. Sci. Technol. A, 1999 17 2401]; (CVD (Chemical Vapor Deposition), or by molecular beams [Philip Moriarty, Nanostructured Materials, Reports on Progress in Physics, 64], 297-381 (2001)] (MBE, Molecular Beam Epitaxy), ion sputtering procedures [J. Musil, I. Leipner, M. Kolega, Surf. Coat. Tech, 115, 32-37, (1999)], etc.

Depending on the type of material obtained these techniques are grouped as epitaxial techniques (MBE, CVD and ablation) and massive techniques (all others). However, one of the main problems encountered when preparing these materials is their tendency to cluster, causing the disappearance of the properties inherent to the nanometric dimensions. In the only instances in which a good control of the microstructure has been achieved (such as in MBE), the quantity of material prepared is very small, which considerably increases the possible manufacturing costs and prevents a viable industrial exploitation. This is the reason that has prompted several groups to dedicate considerable efforts to obtain perfectly dispersed nanocrystals in oxidic matrixes [K. Niihara, "New Design Concept of Structural Ceramics-Ceramic Nanocomposites", J. Ceram. Soc. Jpn. 99 (1991) 974; S. T. Oh, M. Sando and K, Niihara, "Mechanical and magnetic properties of Ni—Co dispersed $Al_2O_3$ nanocomposites", J. Mater. Sci. 36 (2001) 1817; T. Sekino and K. Niihara, "Microstructural characteristics and mechanical properties for $Al_2O_3$/metal nanocomposites", Nanostructural Materials, Vol. 6 (1995) 663; T. Sekino, T. Nakajima, S. Ueda and K. Niihara, "Reduction and Sintering of a Nickel-Dispersed-Alumina Composite and its Properties", J. Am. Ceram. Soc., 80, 5 (1997) 1139; M. Nawa, T. Sekino and K. Niihara, "Fabrication and Mechanical Properties of $Al_2O_3$/Mo Nancomposites", J. Mater. Sci., 29 (1994) 3183; S. T. Oh, T. Sekino and K. Niihara "Fabrication and Mechanical Properties of 5% vol Copper Dispersed Alumina Nanocomposite", J. Eur. Ceram. Soc., 18 (1998) 31; R. Z. Chen and W. H. TUan, "Pressureless Sintering of $Al_2O_3$/Ni Nanocomposites", J. Eur. Ceram. Soc., 19 (1999) 463; K. Niihara, T. Sekino, Y. H. Choa, T. Kusunose, Y. Hayashi, K. Akamatsu, N. Bamba, T. Hirano and S. Ueda "Nanocomposite Structural Ceramics with Advanced Properties", Proc. 4th Japan International SAMPE (1995); K. Niihara, T. Sekino, Y. H. Choa, T. Kusunose, Y. Hayashi, K. Akamatsu, N. Bamba, T. Hirano and S. Ueda, "Nanocomposite Structural Ceramics with Advanced Properties", Proc. 4th Japan International SAMPE. (1995)]. It is in this field where the development of a simple, efficacious and cheap method to prepare metallic nanoparticles is of considerable interest, from the industrial perspective, since it would allow the manufacture of new devices based in the properties of the nanomaterials at very competitive prices.

DESCRIPTION OF THE INVENTION

The objective of the present invention is to overcome most of the obstacles present in the current art by implementing a simple, economic, and viable procedure to prepare nanoparticles at the industrial scale by homogenously dispersing a metallic compound in contact with a support, in which the support is at least a clay with a silicate network selected from the pseudolaminar phyllosilicate clays. According to the present invention, the clay may be a sepiolite clay, including the natural mineral sepiolites and the treated sepiolites such as rheologic grade sepiolite (as those marketed by TOLSA S. A:, Madrid, Spain under the PANGEL brand and obtained from natural sepiolite by special micronization processes that substantially avoid fiber breakage and described, for instance, in the patent applications EP-A-0170299 and EP-A-0454222), mineral or treated attapulgite, such as rheologic grade attapulgite (like the one found in the ATTAGEL product range manufactured and commercialized by Engelhard Corporation in the United States, and the MIN-U-GEL product range offered by the Floridin Company, or those obtained by treating attapulgite with the process described in patent EP-A-0170299). Conveniently, the support is a powder which particle size is smaller than 44 µm and preferably smaller than 5 µm.

Sepiolite and attapulgite or palygorskite belong to the pseudolaminar phyllosilicate clays, also known as palygorskite-sepiolite group, which structure determines a microfibrous or acicular morphology.

Hence, sepiolite is a hydrated magnesic silicate, although there are also aluminic sepiolites (in which 19% of the octahedral positions are occupied by aluminum ions), ferric sepiolites (called xylotile), nickelferrous sepiolites (falcondoite) and sodic sepiolites (loughlinite). Palygorskite, or attapulgite, is a hydrated aluminum magnesium silicate with a structure similar to that of sepiolite. According to Brauner and Preisinger, sepiolite is structurally formed by talcum type strands composed by two layers of silicon tetrahedrons joined by oxygen atoms to a central layer of magnesium octahedrons. These talcum-type strands are arranged in such a manner that the silicon tetrahedral layer is continuous, but the silicon tetrahedrons are inverted at intervals of six units. This structure determines the acicular morphology of the sepiolite particles, elongated along the axis c, and the presence of channels, called zeolitic channels, oriented in the direction of the c axis of the acicular particles and measuring $3.7 Å \times 10^6 Å$, where water and other liquids can penetrate. As a result of this structure, sepiolite has a very high specific surface area that is due not only to the high external surface, but also to the internal surface originated by the zeolitic channels. The theoretical total specific surface of sepiolite, calculated in base to structural models, is of 900 m$^2$/g, of which 400 m$^2$/g belong to the external area and 500 m$^2$/g to the internal area. However, not all of the sepiolite surface is equally accessible to all molecules. The accessible surface of sepiolite depends of the adsorbate used, of its size and of its polarity, which determines the accessibility of the adsorbate molecule to the clay's micropores and the zeolitic channels. The accessible BET surface to N$_2$ is more than 300 m$^2$/g, one of the highest surfaces found in a natural compound.

Attapulgite has a similar structure, although in this case the inversion of the silicon tetrahedrons occurs every other four tetrahedrons, instead of every other six as in the case of sepiolite. As a result, the attapulgite's zeolitic channels have a section of 3.7 Å×6.4 Å, that is, smaller than those of the sepiolite's channels, and therefore, attapulgite's specific surface, at approximately 150 m$^2$/g, although high, is also smaller than that of sepiolite's.

The microfibrous particles of sepiolite and attapulgite are, in their natural state, arranged in clusters that form great bundles of acicular particles randomly arrayed in a structure analogous to that of a haystack. The structure thus formed is very porous and has a high volume of mesopores and macropores. By using special milling and micronization techniques, such as those described in patent EP-A-0170299, it is possible to de-agglomerate these microfiber beams into individual microfibrous particles while maintaining the high "aspect ratio", that is the length/diameter ratio. These procedures allow the adsorbed molecules easier access to the external surface, therefore increasing the surface accessible for adsorbtion. Treating sepiolite and attapulgite thermally in order to eliminate the water adsorbed on the surface, and particularly, the water linked by hydrogen bridges to the water molecules of crystallization that complete the coordination of the magnesium atoms—in the case of the sepiolite- or the magnesium and aluminum atoms—in the attapulgite's a case-located at the edge of the structure, both in the internal zeolitic channels as in the open channels located at the edge of the structure, serves to also increase the adsorption capacity of these clays.

Obtaining metallic nanoparticles over the clay's surface may be done by using any of the paligorskite-sepiolite clays, for instance, sepiolite, attapulgite and their combinations, and sepiolite and/or attapulgite mineral provided they are present in a concentration in which the sum exceeds 50%, and preferably if it is 85%, since the contamination by other minerals such as calcite, dolomite, feldspar, mica, quartz or smectite, besides diluting the clay over which the nanoparticles can form, can also affect the final properties of the product, as well as the development of the process itself, both during the precipitation of salts, hydroxides or oxides, and during the thermal treatment applied for the reduction of the metal.

Also, the metallic compound is, at the least, a precursor selected from the salts, hydroxides and oxides of the metallic elements, and the metallic element is selected from metallic elements susceptible to reduction at temperatures that are below the temperature at which the clay silicate network collapses. Some adequate metallic elements are Fe, Co, Ni, Cu, Mo, Ru, Rh, Pd, Ag, W, Re, Os, Ir, Pt, Au and their alloys or combinations thereof. These metallic elements are present in precursors such as hydrosoluble salts (chlorides, nitrates and sulphates).

The procedure described in the present invention also includes a deposition stage in which the precursor is deposited over the support, and when said precursor has been selected from salts and hydroxides, the procedure also entails a thermal decomposition stage in controlled atmosphere in which the precursor is decomposed into the oxide of the metallic element of choice. Later, a reduction stage is carried out in which the oxide of the metallic element is subject to a complete reduction process under controlled partial oxygen pressure (p0$_2$) and temperature conditions to finally obtain metallic nanoparticles deposited over the support.

The procedure is done at temperatures below that at which the silicate network of the clay would be destroyed, and preferably, at temperatures below 850° C., since at higher temperatures the sepiolite and the attapulgite suffer profound structural transformations that lead to the destruction of the silicate network as well as the potential appearance of other stages, such as clinosteatite, in the case of the vitreous phase of sepiolite.

One of the embodiments of the deposition stage entails dissolving the precursor in water to obtain a dilution of the precursor, disperse the support in said precursor dilution to obtain a precursor/support dispersion, and dry the precursor/support dispersion to obtain dry precursor/support particles. To enhance the degree of dispersion of the clay the preferred method is to apply mechanical stirring with high powered shear blades.

Preferably, and depending on the desired results, the precursor dilution is adjusted to a precursor concentration of 5 to 15%, the support diluted in water or in precursor dilution is adjusted to a 5 to 15% concentration. In addition, and conveniently, the support/precursor dispersion may be adjusted to a metallic element/support ratio in a range from 0.1:100 to 100:100 as a function of the desired density of the nanoparticles to be obtained on the surface of the support, and more preferably within a 5:100 to 50:100 range by weight.

When the aim is to precipitate the precursor over the support by raising the pH of the support/precursor dispersion this is achieved a base before the drying stage. The precipitation of precursors must be done in a controlled manner in order for the particles to deposit homogeneously over the clay's surface.

Also, the precursor/support dispersion is filtered before proceeding to the drying stage, and/or is separated by solid/liquid separation techniques before the drying stage. Preferably, a filtration or liquid/solid separation is done to separate the clay the metallic precursors deposited over the surface of the solution containing the metallic salt ion used, although a direct drying can be done to evaporate all the water present in the dispersion. In some cases when the separation is done by filtering to separate the clay the metallic precursors deposited, it is recommended to wash the clay to eliminate any trace of the soluble salt. The next step is the thermal treatment carried out under controlled atmosphere conditions to effect the decomposition of the metallic salts or hydroxides in the appropriate oxide, provided the precursor deposited over the clay is not said oxide; the next step is the reduction of the metal oxide in the appropriate metal. The conditions for the reduction (temperature and partial oxygen pressure) will depend on the metallic element used.

Utilizing the techniques described above, it is possible to obtain monodispersed metallic nanoparticles deposited over the support, always in a size smaller than 30 nm, and very frequently it is possible to obtain controlled sizes between 10 nm and 5 nm, and thus form a nanoparticulate "nanocomposite" material useful for a diversity of applications. Thus, when the metallic element has been selected from Cu, Ag, Au, Rh, Pd, Ir, Ni, Pt and combinations thereof, the nanoparticulate "nanocomposite" material is useful as such, or as a component of a catalyst, while when the metallic element selected is Ag, the nanoparticulate "nanocomposite" material is useful as a biocide or as a component of biocides. In the same manner, when the metallic element selected is Cu, the nanoparticulate "nanocomposite" material is useful as fungicide or as a component of fungicide products.

Also, when the metallic element has been selected from Cu, Ag, Au and combinations thereof, the nanoparticulate "nanocomposite" material is useful as component of optoelectronic materials, while when the metallic element has been selected from Fe, Ni, Co and combinations thereof the nanoparticulate "nanocomposite" material is useful as component of ferromagnetic fluids.

In this process the clay used may have any particle size, although when the nanoparticles are formed on the clay particle's surface, it is advisable to use a clay product with the smallest possible particle size in order for the surface of the particle accessible to nanoparticles formation to be the maximum possible size. In this manner the clay can be added as milled powder with a particle size smaller than 44 µm. Rheologic grade products such as rheologic grade sepiolite can also be used, as obtained by means of a wet micronization processes such as those described in the patent application EP-A-0170299, with which free acicular particles have been obtained while maintaining the high "aspect ratio" of the particles, and where the de-agglomeration process has left more free surface accessible to deposition. In addition, the colloidal properties of the clays treated according to this micronization process have higher stability and disperse better in the metallic salt dilution, allowing for a more homogenous coating.

The information described above indicates that the procedure described in the present invention is based on the deposition over the surface of these metallic salts, oxides or hydroxide clays, followed by a reduction treatment intended to obtain the corresponding metals. The reduction process is done by means of a thermal treatment carried out under controlled atmosphere conditions. It can be noted that the size of the nanoparticles formed by this process is smaller than 30 nm, and normally a size of approximately 3 nm, with a homogeneous distribution over the surface and not clustered. The nanoparticles are distributed linearly and oriented along the longitudinal axis of the microfibrous particles. A possible explanation for the formation of the metallic nanoparticles in this particular arrangement may be the transformations undergone by the sepiolite and the attapulgite during thermal treatments. At 350° C. the sepiolite losses two of the four molecules of hydration water, producing the folding of the sepiolite's structure, and the collapse of the zeolitic channels in order for the cations located at the edge of the octahedral layer of the silicate to complete their coordination with the oxygen molecules of the tetrahedral layer of the adjacent silicon. This change is reversible. The original structure can be recovered by rehydrating the sepiolite. At a temperature of 500° C., the sepiolite losses the two remaining water molecules of crystallization, and although there are no additional structural changes, the folding of the structure becomes at this point irreversible. The attapulgite suffers a similar structural change during thermal treatment. It is believed that during the thermal treatment carried out to decompose the metal salts or hydroxides in their corresponding oxides, and the subsequent step of reducing the metallic oxides particles, these particles are trapped during the folding and collapsing of the open channels located at the edge of the structures, preventing the migration of the metallic nanoparticles and their coalescence and growth processes that would form particles of greater size. As a consequence, it is possible to obtained monodispersed nanoparticles which size is smaller than 30 nm that can be controlled as a function of the impregnation conditions for the metallic salts, hydroxides and oxides, and as a function of the reduction conditions, to obtain a controlled particle size that can be maintained between 10 nm and 5 nm, and even to obtain particle sizes smaller than 5 nm. This mechanism explains the linear arrangement of the nanoparticles along the axis of the microfibrous particle, following the open channels located at the edge of the structure over the surface of the acicular particle.

BRIEF DESCRIPTION OF THE DRAWINGS

This section contains the description of some examples of the embodiments of the invention that will be referred to the following figures:

FIG. 1a is a microphotograph of copper nanoparticles supported over sepiolite and obtained according to the method described in Example 1;

FIG. 1b is a less enlarged microphotograph of the nanoparticles supported over sepiolite and also obtained according to the method described in Example 1;

EXAMPLES OF THE DIFFERENT
EMBODIMENTS OF THE INVENTION

Example 1

The procedure begins by preparing one liter of copper dissolution (28, 51 g of copper nitrate per liter), for a theoretical impregnation level of 5%. Then the dissolution is acidified to pH 2 to insure the copper salt is dissolved.

A dispersion of micronized sepiolite in water is prepared in a mixer, in which the size of 99.9% of the particles is smaller than 44 μm and the size of 95% is smaller than 5 μm. The concentration of the dispersion is 10% solids (150 g of dry sepiolite base for 1,500 g of pregel), and the dispersion mixed during 5 minutes by means of a mechanical stirrer. This predispersion of clay, which pH is approximately 9.0 is then acidified to pH 2 and then the copper dilution is added and the mixture stirred for an additional 5 minutes to ensure the contact between the dilution and the sepiolite is complete. The sepiolite dispersion in the copper dilution has a sepiolite concentration of 6%.

Figure 2A:
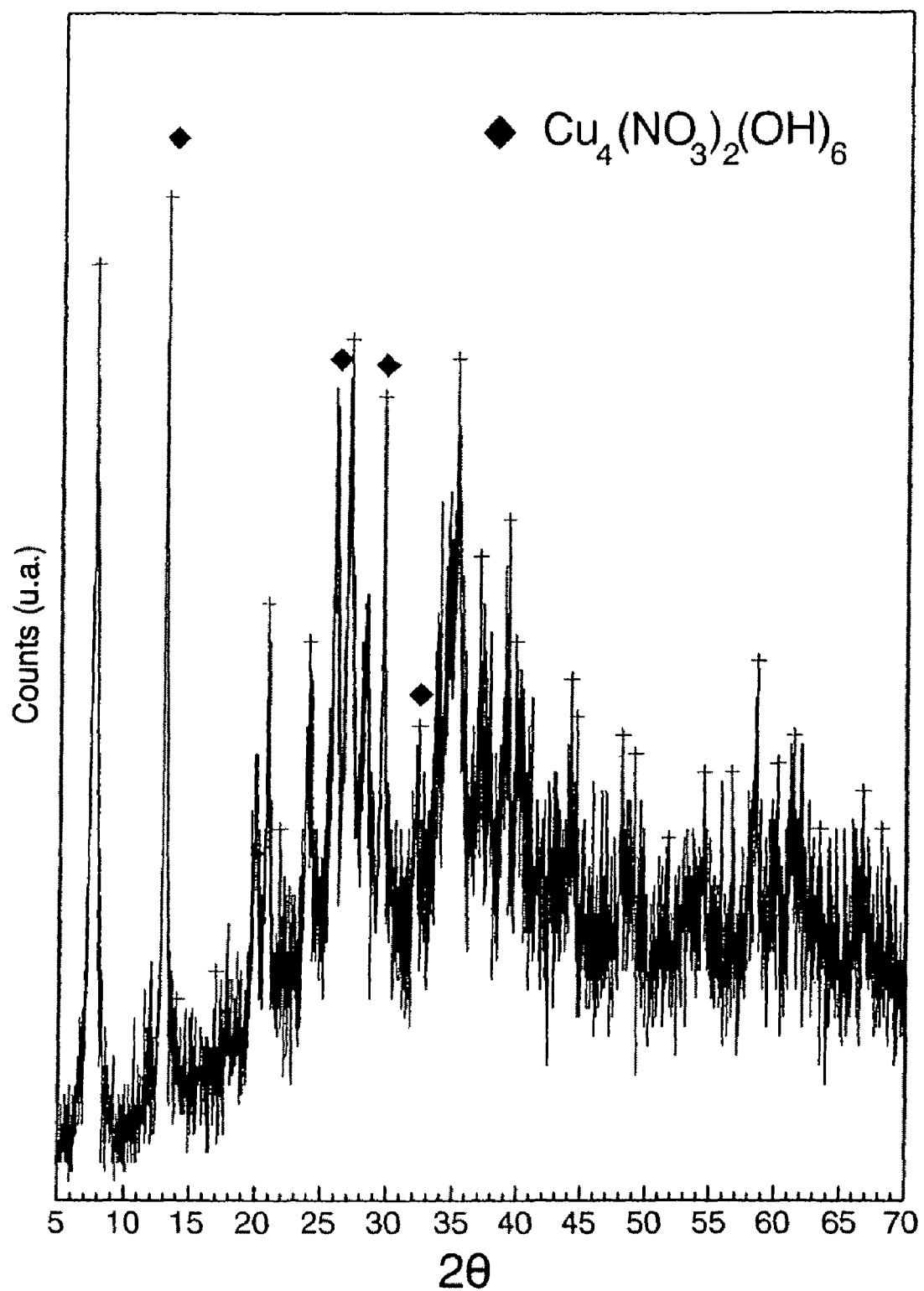
FIG. 2a is an X-ray diffractogram showing copper precipitated as gerhardite over the sepiolite support according to Example 1.

Later, the copper precipitates as gerhardite (Cu, $(NO_3)_2$ $(OH)_6$) (FIG. 2a), by adding 1M sodium hydroxide until reaching a final pH=5.3. The sodium hydroxide dilution is added slowly while the mixture is being mechanically stirred. Once the copper hydroxide has precipitated the dispersion is filtered in a vacuum, washed and oven dried at 150° C. During this process it was observed that the BET specific surface of the sepiolite was reduced from 439 to 121 $m^2/g$.

The sepiolite with the precursor is then subject to a reduction process in a tubular section oven with a controlled atmosphere of 10% $H_2$/90% Ar. The oven is outfitted with a programming device to control the temperature (±1° C.). The reduction cycle entails heating the mixture in increasing intervals of 10° C./min until reaching a temperature of 500° C. that is maintained for 2 hours, followed by a free cooling period inside the oven.

As a result of this process, small copper nanoparticles are obtained over the sepiolite fibers support. The nanoparticles appear monodispersed and arranged parallel to the direction of the sepiolite fibers as can be observed in the attached microphotographs (FIG. 1a and FIG. 1b).

Finally, the calcination process, that is carried out in a $H_2$ atmosphere, further decreases the surface until it reaches a value of 87 $m^2/g$.

Figure 2B:
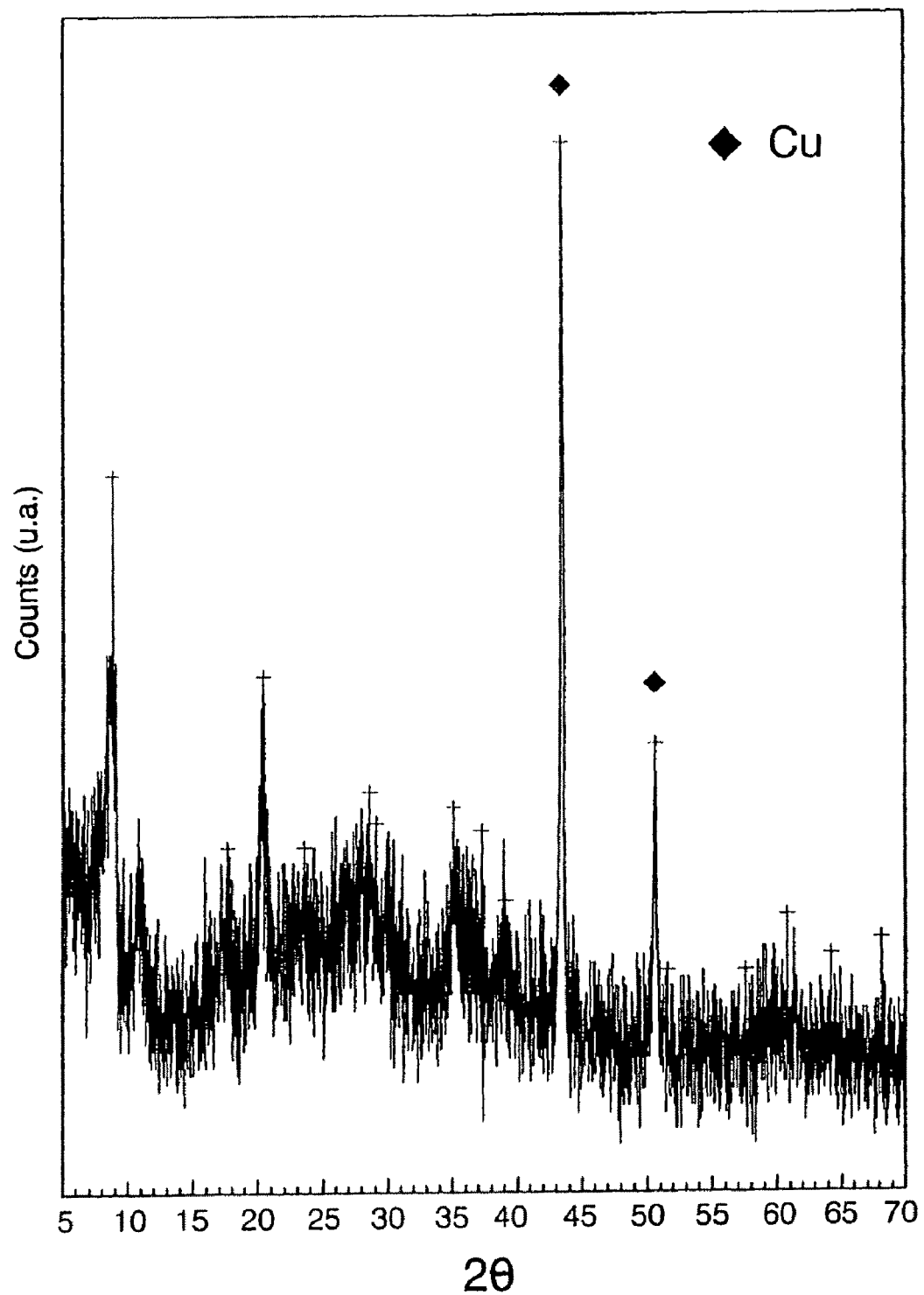
FIG. 2b is an X-ray diffractogram of the final product according to Example 1.

The X-ray diffractogram of the reduced sample shows that the material is indeed composed of sepiolite and metallic copper (FIG. 2b).

Figure 3:
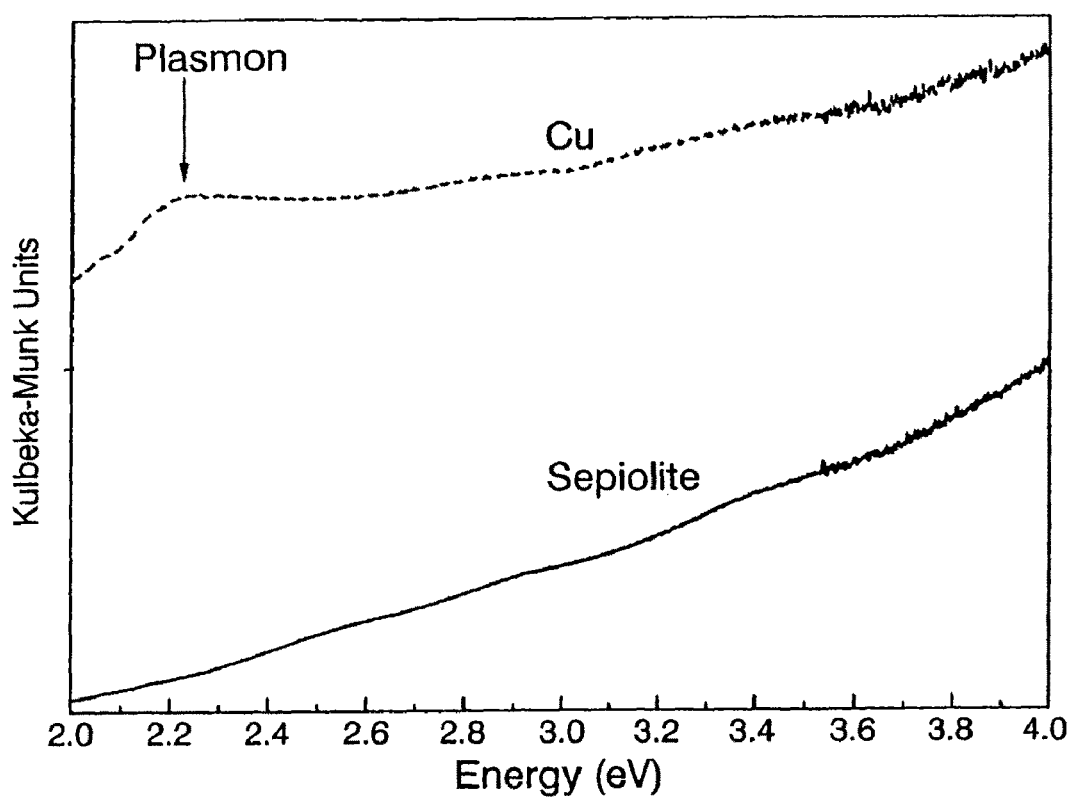
FIG. 3 shows the absorbance spectrum expressed in Kulbeka-Munk units measured by diffuse reflectance of the final product obtained as per Example 1.

Additional evidence of the metallic nature of the nanoparticles thus obtained, as well as their dispersion pattern, was obtained by analyzing the diffuse reflectance spectra within the visible ultraviolet range. When a metal finely divided (of a size smaller than the wavelength) and dispersed interacts with the electromagnetic radiation, it presents a well defined frequency, a collective electron excitation phenomenon known as surface plasmon [C. F. Bohren and D. R. Huffman, "Absorption and Scattering of Light by Small Spheres", Ed. John Wiley and Sons, New York, 1983, pages 325 on]. In the frequency at which this phenomenon occurs, it is verified that the real part of the dielectric constant of the metal is equal to minus two times the dielectric constant of the matrix ($_E$(w)=− $2_{Em}$). Since this frequency, which can be experimentally recognized by an absorption maximum, is specific to each metal, it has served us as identification of the metallic nature of the nanoparticles. In the case of copper, the experimental spectrum shows a maximum absorption at 2.2. eV (FIG. 3) which is consistent with the value that would correspond to copper nanoparticles in air ["Handbook of Optical Constants of Solids", Edited by E. D. Palik, Academic Press, 1985, Orlando, USA].

Example 2

A silver dilution containing 35.45 g of silver nitrate per liter is prepared and then acidified to pH=2 using $NO_3H$. A sepiolite predispersion with a 10% concentration of solids is then added to the silver nitrate dilution. The sepiolite predispersion is prepared by dispersing the sepiolite during 5 minutes in a mechanical stirrer with high powered shear blades to insure a good dispersion of the clay particles. The sepiolite used in this example is a PANGEL rheologic grade sepiolite manufactured by TOLSA S.A. Once the sepiolite predispersion has been added to the silver nitrate dilution for the Ag/sepiolite relationship to be in a 15/100 ratio, the mixture is stirred at high shear setting during 5 more minutes and it is then, while still stirring, a 1M NaOH solution is added slowly until pH=12. Increasing the pH produces the precipitation of the silver precursor that is then deposited homogeneously over the sepiolite's surface. Later, the dispersion is filtered in a vacuum and oven dried at 150° C.

During this process, the BET specific surface of the sepiolite is decreased from 439 to 204 $m^2/g$.

Figure 5A:
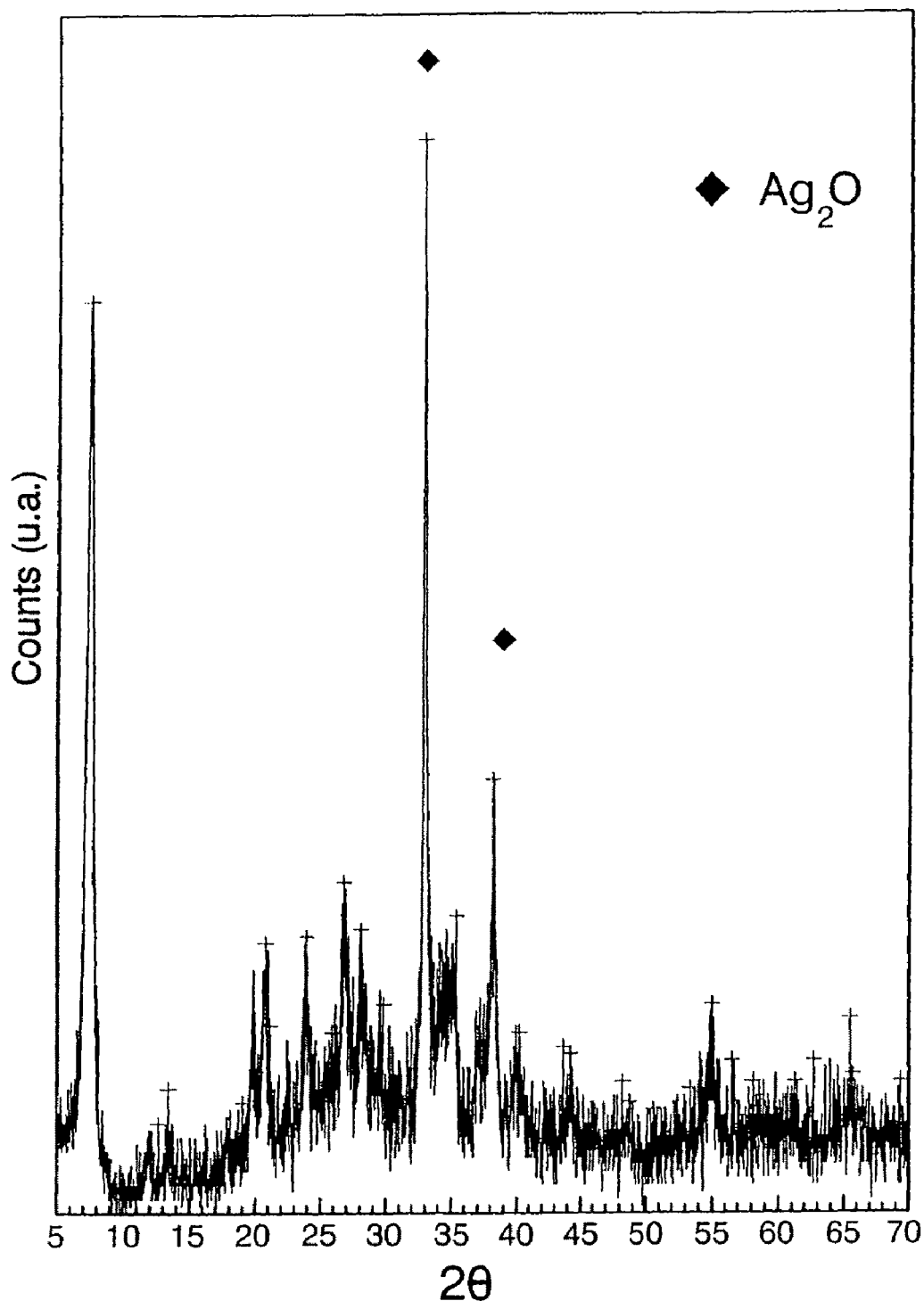
FIG. 5a is an X-ray diffractogram showing silver oxide precipitated over the sepiolite support according to Example 2.

The sepiolite with the silver precursor ($Ag_2O$ in this particular instance) (FIG. 5a) is subjected to a reduction process in a tubular sectioned oven similar to that described in the previous case and the temperature is set at 400° C.

Figure 4A:
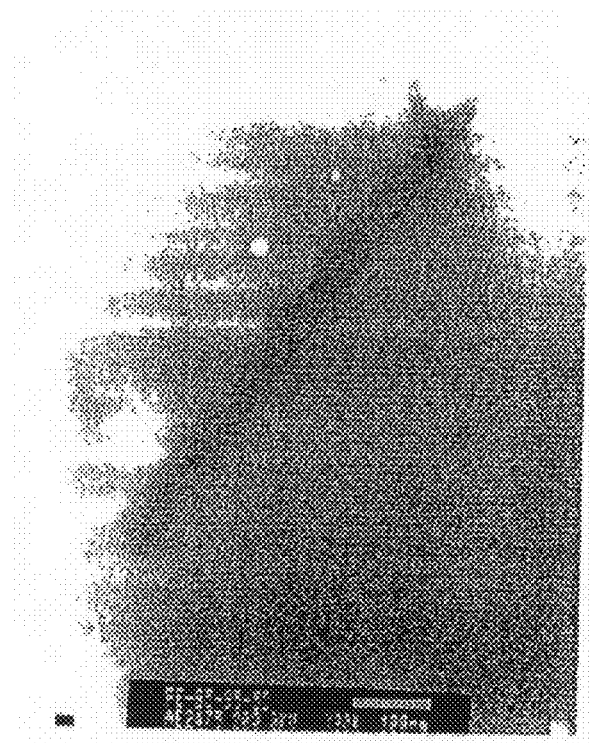
FIG. 4a is a microphotograph of silver nanoparticles supported over sepiolite and obtained according to the method described in Example 2.
Figure 4B:
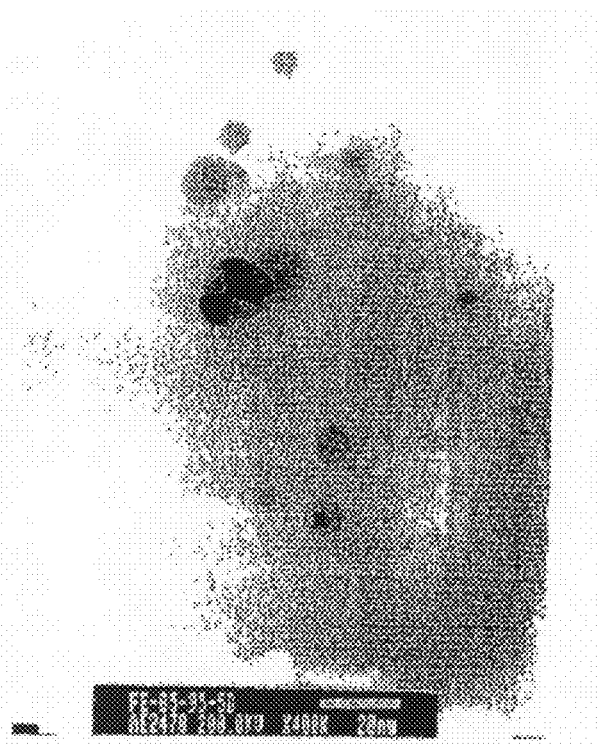
FIG. 4b is a less enlarged microphotograph of the nanoparticles supported over sepiolite and obtained according to the method described in Example 2.

The particles obtained as a result of this process are elongated sepiolite particles over which small silver nanoparticles have appeared following the direction parallel to the long axis of the sepiolite fibers. An image of these particles can be seen in FIG. 4a and FIG. 4b. In this case some particles of about 15 nm can be seen together with small nanoparticles of a few nm.

Once the silver oxide particles have been reduced, the final specific surface of the powder has decreased to 112 $m^2/g$.

Figure 5B:
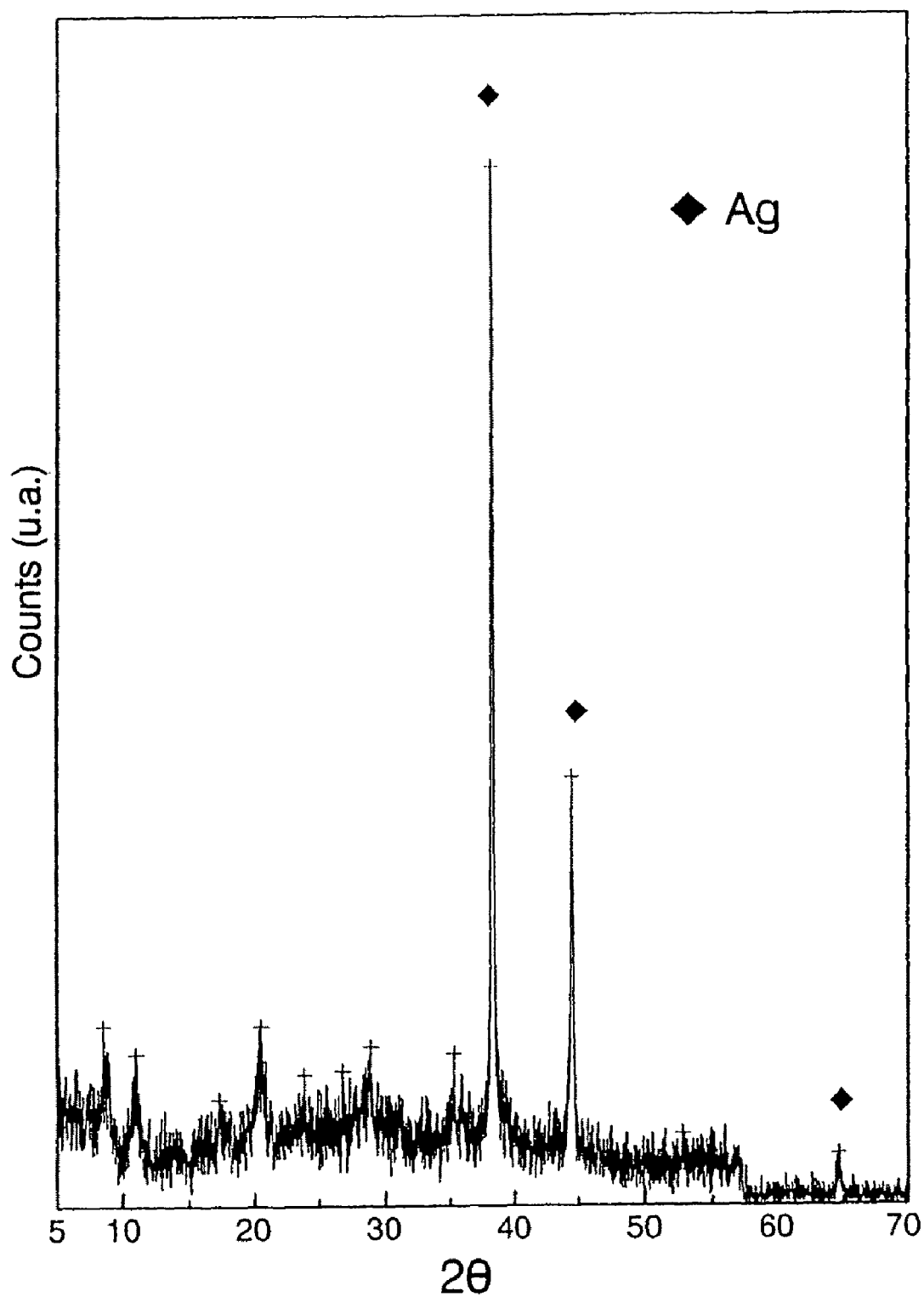
FIG. 5b is an X-ray diffractogram showing the final product according to Example 2.

The X-ray diffractogram of the reduced sample shows that the material is indeed composed of sepiolite and silver (FIG. 5b).

Figure 6:
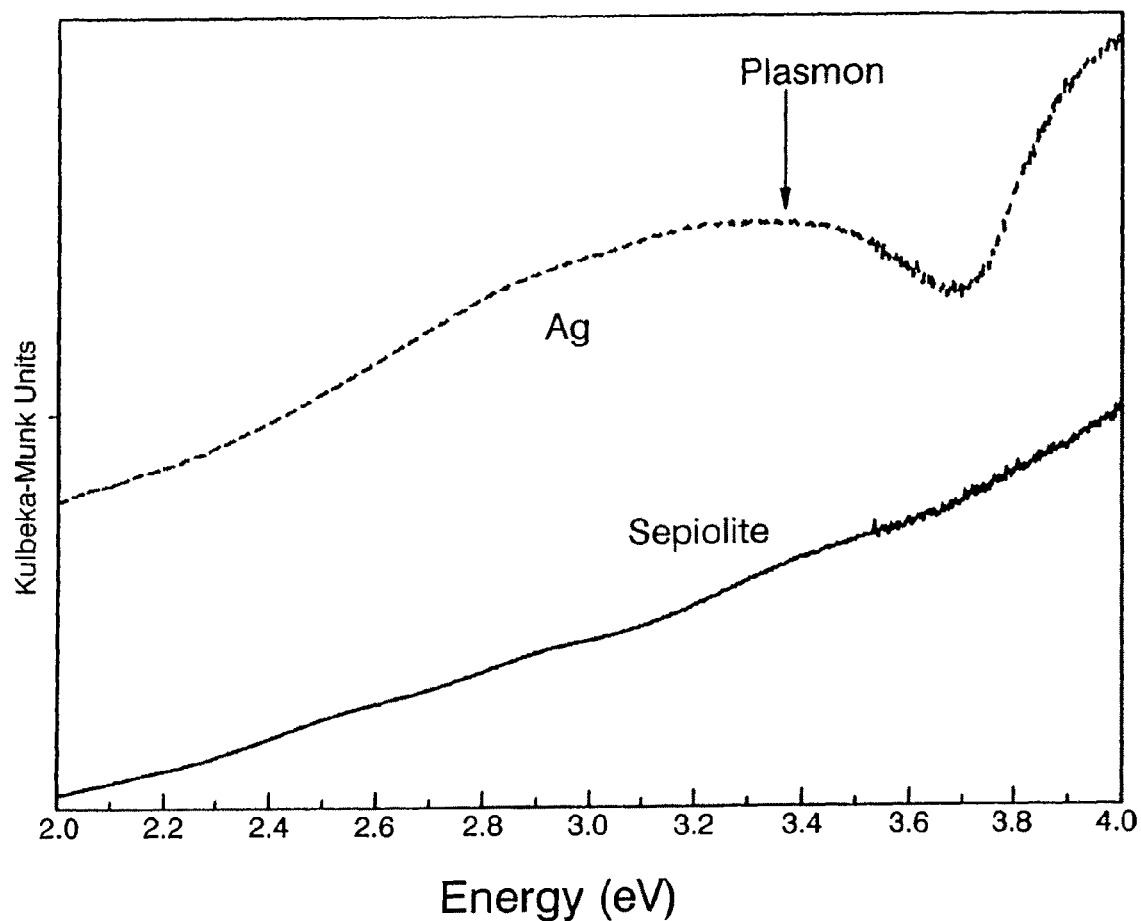
FIG. 6 shows the absorbance spectrum in Kulbeka-Munk units measured by diffuse reflectance of the final product obtained according to Example 2.

In the same manner as in the prior example, the optic absorption of sepiolite samples with silver was measured in Kulbeka-Munk units by means of diffuse reflectance in the visible range of ultraviolet light. In this case the plasmon was also visible, but at a higher frequency (3.4 eV) and showing an irregular aspect as it is the case for silver nanoparticles (FIG. 6).

Example 3

Figure 8A:
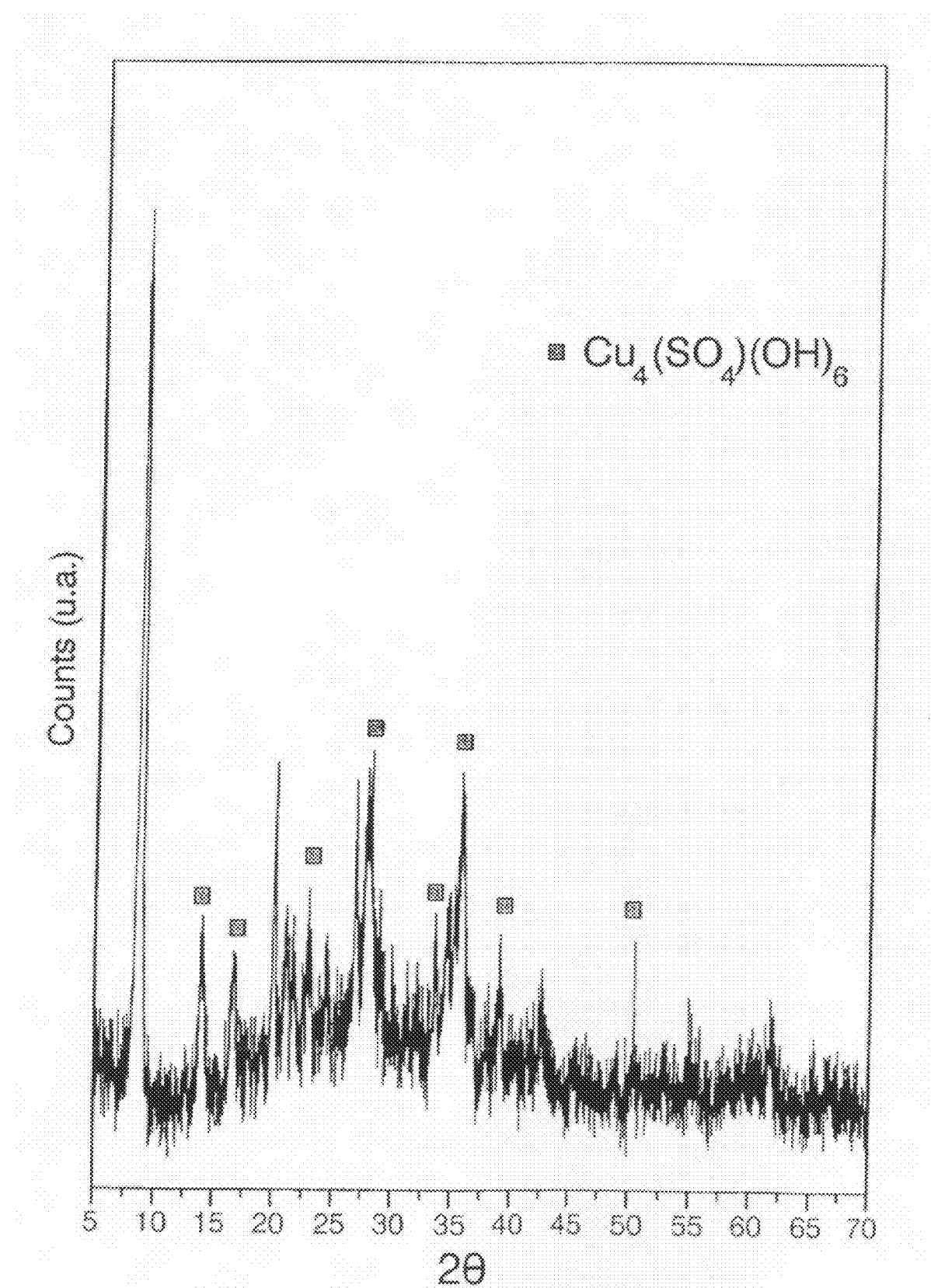
FIG. 8a is an X-ray diffractogram showing copper precipitated as copper hydroxide sulphate over the attapulgite support according to Example 3.

A copper sulfate solution containing 79.11 g of copper sulfate per liter is first prepared and then acidified by adding $SO_4H_2$ until obtaining a pH value of 2. Later a predispersion of attapulgite in which the solids concentration=10% is added. The attapulgite predispersion is prepared by dispersing the attapulgite during 5 minutes in a mechanical stirrer with high powered shear blades to insure a good dispersion of the clay particles. The attapulgite used is an ATTAGEL 40 from the Engelhard Corporation that has been micronized in wet conditions according to the procedure described in patent EP-A-0170299. Once the attapulgite predispersion has been added to the copper sulfate dilution for the Cu/attapulgite relationship to be in a 15/100 ratio, the mixture is stirred at high shear setting during 5 more minutes and, while still stirring, a 1M NaOH solution is added slowly until pH=5.5. Increasing the pH produces the precipitation of one phase of the copper hydroxide sulfate (FIG. 8a) that then deposits homogeneously over the attapulgite's surface. Later, the dispersion is filtered in a vacuum and oven dried at 150° C.

The attapulgite with the precursor is subjected to a reduction process in a tubular sectioned oven under controlled atmosphere conditions of 10% $H_2$/90% Ar. The reduction cycle is a heating process in which temperature is increased at 10° C./min until reaching a final temperature of 500° C. which is maintained during 2 hours and followed by a free cooling period inside the oven.

Figure 7A:
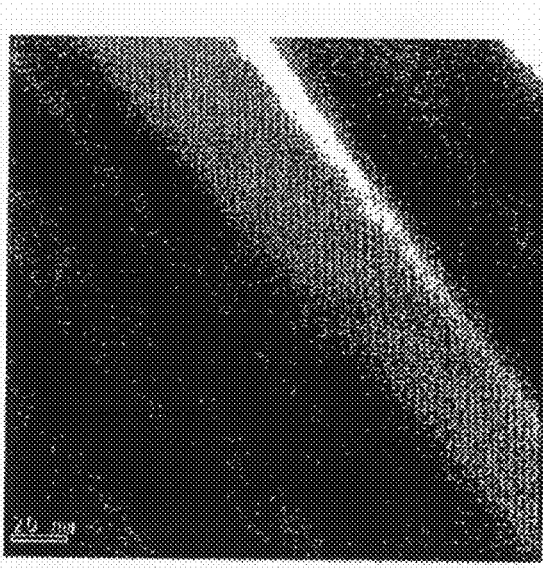
FIG. 7a is a microphotograph of copper nanoparticles supported over attapulgite and obtained according to the method described in Example 3.
Figure 7B:
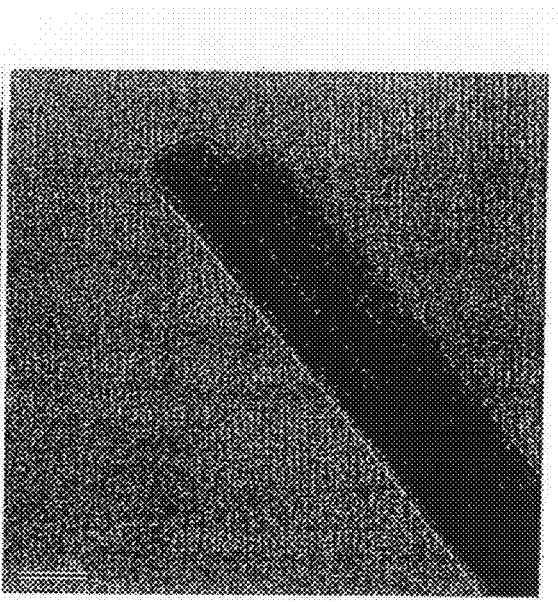
FIG. 7b is a less enlarged microphotograph of the nanoparticles supported over attapulgite and obtained according to the method described in Example 3.

The particles obtained as a result of this process, are copper nanoparticles supported by attapulgite fibers. In this case acicular nanoparticles appear in a parallel arrangement following the direction of the attapulgite fiber. Their size is approximately 30 nm long by a few nm wide (FIG. 7b). When observing them in depth, it can be seen that these nanoparticles are made by nanoparticles clusters of approximately 3 nm.

Figure 8B:
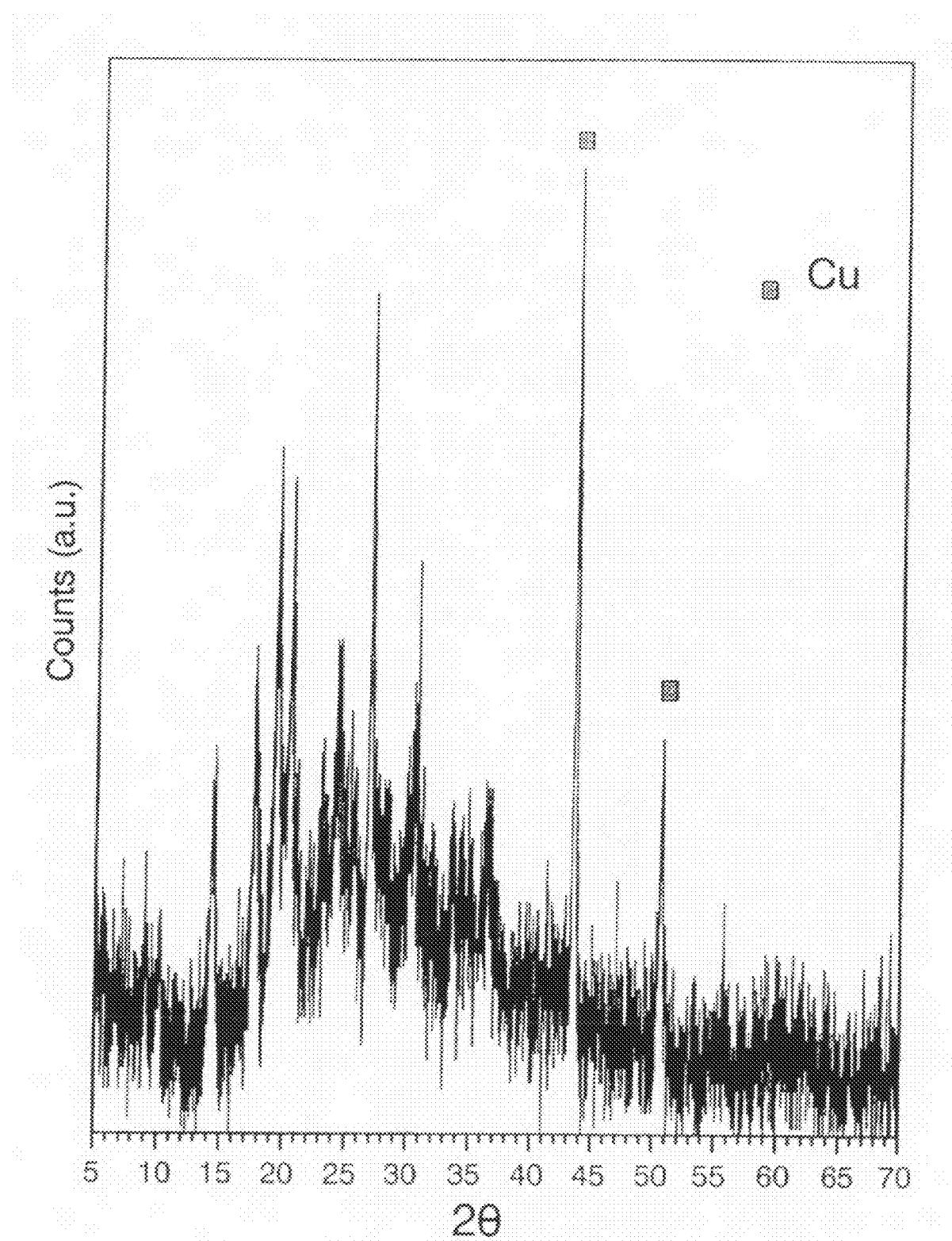
FIG. 8b is an X-ray diffractogram showing the final product according to Example 3.

The X-ray diffractogram of the reduced sample shows that the material is indeed composed of attapulgite and metallic copper (FIG. 8b).

While the invention has been described and illustrated herein by reference to the specific embodiments, various specific materials, procedures and examples, it is understood that the invention is not restricted to the particular materials, combinations of materials, and procedures selected for that purpose. Indeed, various modifications of the invention in addition to those described herein will become apparent to those skilled in the art from the foregoing description and the accompanying figures. Such modifications are intended to fall within the scope of the appended claims.

The invention claimed is:

1. A compound material that is composed of metallic nanoparticles deposited on the surface of a support, said metallic nanoparticles being obtained by a method, in which
the support is at least one clay possessing a silicate network and selected from sepiolite and attapulgite, a metallic precursor is at least a precursor selected from salts, hydroxides and oxides of metallic elements,
the metallic element is selected from metallic elements susceptible to reduction at temperatures below the destruction temperature of the silicate network of the clay, and wherein the method also comprises,
an acidification stage of the metallic precursor,
a deposition stage in which the precursor deposits on the support,
a thermal decomposition stage, when the precursor is selected from salts and hydroxides, that is carried out under controlled atmosphere conditions in which the precursor is subjected to a decomposition treatment during which the precursor is transformed into an oxide of the metallic element, and
a thermal reduction stage carried out under controlled conditions in which the oxide of the metallic element is subjected to a reduction process in order to obtain nanoparticles of the metallic element deposited on the support,
the procedure is carried out at temperatures below the destruction temperature of the clay's silicate network and results in the obtaining of metallic nanoparticles with a particle size smaller than 30 nm.

2. A compound material according to claim 1 wherein the metallic nanoparticles are homogeneously dispersed over a support, and in which said support is at least one clay, possessing a silicate network, that has been selected from sepiolite and attapulgite,
in which the metallic nanoparticles are particles from an element selected from Fe, Co, Ni, Cu, Mo, Ru, Rh, Pd, Ag, W, Re, Os, Ir, Pt, Au and alloys thereof, and
in which the size of said metallic nanoparticles is smaller than 30 nm.

3. A catalyst comprising a compound material of metallic nanoparticles deposited on the surface of a support, being said compound obtained by a method, in which
the support is at least one clay possessing a silicate network and selected from sepiolite and attapulgite, the metallic precursor is at least a precursor selected from salts, hydroxides and oxides of metallic elements,
the metallic element is selected from metallic elements susceptible to reduction at temperatures below the destruction temperature of the silicate network of the clay, and wherein the method also comprises,
an acidification stage of the metallic precursor,
a deposition stage in which the precursor deposits on the support,
a thermal decomposition stage, when the precursor is selected from salts and hydroxides, that is carried out under controlled atmosphere conditions in which the precursor is subjected to a decomposition treatment during which the precursor is transformed into an oxide of the metallic element, and
a thermal reduction stage carried out under controlled conditions in which the oxide of the metallic element is subjected to a reduction process in order to obtain nanoparticles of the metallic element deposited on the support,
the procedure is carried out at temperatures below the destruction temperature of the clay's silicate network and results in the obtaining of metallic nanoparticles with a particle size smaller than 30 nm.

4. A catalyst according to claim 3 wherein the metallic element is selected from Cu, Ag, Au, Rh, Pd, Ir, Ni, Pt, and combinations thereof.

5. A biocide material comprising a compound of metallic nanoparticles deposited on the surface of a support, being said metallic nanoparticles obtained by a method in which
the support is at least one clay possessing a silicate network and selected from sepiolite and attapulgite, the metallic precursor is at least a precursor selected from salts, hydroxides and oxides of metallic elements, the metallic element is selected from metallic elements susceptible to reduction at temperatures below the destruction temperature of the silicate network of the clay, and wherein the method also comprises, an acidification stage of the metallic precursor, a deposition stage in which the precursor deposits on the support, a thermal decomposition stage, when the precursor is selected from salts and hydroxides, that is carried out under controlled atmosphere conditions in which the precursor is subjected to a decomposition treatment during which the precursor is transformed into an oxide of the metallic element, and a thermal reduction stage carried out under controlled conditions in which the oxide of the metallic element is subjected to a reduction process in order to obtain nanoparticles of the metallic element deposited on the support, the method is carried out at temperatures below the destruction temperature of the clay's silicate network and results in the obtaining of metallic nanoparticles with a particle size smaller than 30 nm, and wherein the metallic element is Ag.

6. A fungicide material comprising a compound material of metallic nanoparticles deposited on the surface of a support, being said metallic nanoparticles obtained by a method in which the support is at least one clay possessing a silicate network and selected from sepiolite and attapulgite, the metallic precursor is at least a precursor selected from salts, hydroxides and oxides of metallic elements, the metallic element is selected from metallic elements susceptible to reduction at temperatures below the destruction temperature of the silicate network of the clay, and wherein the method also comprises, an acidification stage of the metallic precursor, a deposition stage in which the precursor deposits on the support, a thermal decomposition stage, when the precursor is selected from salts and hydroxides, that is carried out under controlled atmosphere conditions in which the precursor is subjected to a decomposition treatment during which the precursor is transformed into an oxide of the metallic element, and a thermal reduction stage carried out under controlled conditions in which the oxide of the metallic element is subjected to a reduction process in order to obtain nanoparticles of the metallic element deposited on the support, the method is carried out at temperatures below the destruction temperature of the clay's silicate network and results in the obtaining of metallic nanoparticles with a particle size smaller than 30 nm, and wherein the metallic element is Cu.

7. An optoelectronic material comprising a compound material of metallic nanoparticles deposited on the surface of a support, being said metallic nanoparticles obtained by a method, in which the support is at least one clay possessing a silicate network and selected from sepiolite and attapulgite, the metallic precursor is at least a precursor selected from salts, hydroxides and oxides of metallic elements, the metallic element is selected from metallic elements susceptible to reduction at temperatures below the destruction temperature of the silicate network of the clay, and wherein the method also comprises, an acidification stage of the metallic precursor, a deposition stage in which the precursor deposits on the support, a thermal decomposition stage, when the precursor is selected from salts and hydroxides, that is carried out under controlled atmosphere conditions in which the precursor is subjected to a decomposition treatment during which the precursor is transformed into an oxide of the metallic element, and a thermal reduction stage carried out under controlled conditions in which the oxide of the metallic element is subjected to a reduction process in order to obtain nanoparticles of the metallic element deposited on the support, the method is carried out at temperatures below the destruction temperature of the clay's silicate network and results in the obtaining of metallic nanoparticles with a particle size smaller than 30 nm, and wherein the metallic element is selected, from Cu, Ag, Au and combinations thereof.

8. A ferromagnetic fluid comprising a compound material of metallic nanoparticles deposited on the surface of a support, being said metallic nanoparticles obtained by a method in which the support is at least one clay possessing a silicate network and selected from sepiolite and attapulgite, the metallic precursor is at least a precursor selected from salts, hydroxides and oxides of metallic elements, the metallic element is selected from metallic elements susceptible to reduction at temperatures below the destruction temperature of the silicate network of the clay, and wherein the method also comprises, an acidification stage of the metallic precursor, a deposition stage in which the precursor deposits on the support, a thermal decomposition stage, when the precursor is selected from salts and hydroxides, that is carried out under controlled atmosphere conditions in which the precursor is subjected to a decomposition treatment during which the precursor is transformed into an oxide of the metallic element, and a thermal reduction stage carried out under controlled conditions in which the oxide of the metallic element is subjected to a reduction process in order to obtain nanoparticles of the metallic element deposited on the support, the method is carried out at temperatures below the destruction temperature of the clay's silicate network and results in the obtaining of metallic nanoparticles with a particle size smaller than 30 nm, and wherein the metallic element has been selected from Fe, Ni, Co and combinations thereof.

* * * * *